(12) United States Patent
Sato et al.

(10) Patent No.: US 7,942,815 B2
(45) Date of Patent: May 17, 2011

(54) ENDOSCOPE INSERTION PORTION WITH A TWO WIRE BENDING PORTION

(75) Inventors: Eijiro Sato, Hachioji (JP); Kaoru Tsuruoka, Kawasaki (JP)

(73) Assignee: Olympus Medical Systems Corp. (JP)

( * ) Notice: Subject to any disclaimer, the term of this patent is extended or adjusted under 35 U.S.C. 154(b) by 816 days.

(21) Appl. No.: 11/765,854

(22) Filed: Jun. 20, 2007

(65) Prior Publication Data
US 2007/0299311 A1 Dec. 27, 2007

(30) Foreign Application Priority Data

Jun. 23, 2006 (JP) ................................. 2006-173982

(51) Int. Cl.
*A61B 1/00* (2006.01)
(52) U.S. Cl. ......... 600/139; 600/130; 600/146; 600/149
(58) Field of Classification Search .................. 600/139, 600/141, 142
See application file for complete search history.

(56) References Cited

U.S. PATENT DOCUMENTS

| | | | |
|---|---|---|---|
| 5,005,558 A | 4/1991 | Aomori | |
| 6,302,841 B1 | 10/2001 | Hatori | |
| 2002/0032371 A1 | 3/2002 | Torii | |
| 2002/0091304 A1 | 7/2002 | Ogura et al. | |
| 2004/0172018 A1 | 9/2004 | Okada | |
| 2004/0249367 A1* | 12/2004 | Saadat et al. | 606/1 |

FOREIGN PATENT DOCUMENTS

| | | |
|---|---|---|
| EP | 1 090 581 A1 | 4/2001 |
| EP | 1 604 607 A1 | 12/2005 |
| EP | 1 661 505 A1 | 5/2006 |
| JP | 56-124401 | 2/1980 |
| JP | 63-309234 | 12/1988 |
| JP | 4-13101 | 2/1992 |
| JP | 2000-296103 | 10/2000 |
| JP | 2002-320587 | 11/2002 |
| JP | 2006 068393 | 3/2006 |

OTHER PUBLICATIONS

Letter from German associate dated Oct. 30, 2007 forwarding the Search Report dated Oct. 8, 2007 to Japanese associate, including discussion of relevancy thereof.
Search Report issued by European Patent Office on Oct. 8, 2007 in connection with corresponding European patent application No. EP 07 01 2210.
English translation of Japanese Office Action dated Jul. 1, 2008 corresponding to Japanese Patent Application No. 2006-173982.

* cited by examiner

*Primary Examiner* — Matthew J Kasztejna
(74) *Attorney, Agent, or Firm* — Ostrolenk Faber LLP

(57) ABSTRACT

An endoscope insertion portion includes a distal end side wire guide which is provided over a distal end side of a operation wire, and a portion of which is fixed to a bending portion, a proximal end side wire guide which is provided over a proximal end side of a operation wire, and a portion of which is fixed to a insertion tube portion, a distal end side abutting portion provided at a proximal end of the distal end side wire guide, and a proximal end side abutting portion which is provided at a distal end of the proximal end side wire guide, and brought into abutment with the distal end side abutting portion when the operation wire is moved backward so that the bending portion is bent.

12 Claims, 4 Drawing Sheets

ENDOSCOPE INSERTION PORTION WITH A TWO WIRE BENDING PORTION

CROSS-REFERENCE TO RELATED APPLICATIONS

This application is based upon and claims the benefit of priority from prior Japanese Patent Application No. 2006-173982, filed Jun. 23, 2006, the entire contents of which are incorporated herein by reference.

BACKGROUND OF THE INVENTION

1. Field of the Invention

The present invention relates to an endoscope insertion portion including a bending portion to be operated to be bent.

2. Description of the Related Art

An endoscope insertion portion is formed by connecting a distal end rigid portion, a bending portion to be operated to be bent, and a long insertion tube portion, sequentially from the distal end side. An operation wire to be operated to be moved forward and backward to operate the bending portion to be bent is inserted through the insertion portion. The operation wire is inserted through a wire guide in at least the insertion tube portion, and prevents damage of built-in members caused by friction with the operation wire.

In the endoscope disclosed in Jpn. Pat. Appln. KOKAI Publication No. 2006-68393, the wire guide is extended from the insertion tube portion into the bending portion, and the distal end of the wire guide is fixed in the bending portion. When bending the bending portion by moving the operation wire backward, the wire guide functions as a tension rod and prevents bending of the bending portion. Namely, in the bending portion, a part provided with the wire guide is not bent, and a part not provided with the wire guide is bent.

BRIEF SUMMARY OF THE INVENTION

In an aspect of the present invention, an endoscope insertion portion includes: an insertion tube portion; a bending portion which is connected to a distal end of the insertion tube portion, and is operated to be bent; an operation wire which is inserted through the bending portion and insertion tube portion, and is operated to be moved forward and backward to operate the bending portion to be bent; a distal end side wire guide which is provided over a distal end side of the operation wire, and a portion of which is fixed to the bending portion; a proximal end side wire guide which is provided over a proximal end side of the operation wire, and a portion of which is fixed to the insertion tube portion; a distal end side abutting portion provided at a proximal end of the distal end side wire guide; and a proximal end side abutting portion which is provided at a distal end of the proximal end side wire guide, and brought into abutment with the distal end side abutting portion when the operation wire is moved backward so that the bending portion is bent.

In another aspect of the present invention, an endoscope includes the endoscope insertion portion including: an insertion tube portion; a bending portion which is connected to a distal end of the insertion tube portion, and is operated to be bent; an operation wire which is inserted through the bending portion and insertion tube portion, and is operated to be moved forward and backward to operate the bending portion to be bent; a distal end side wire guide which is provided over a distal end side of the operation wire, and a portion of which is fixed to the bending portion; a proximal end side wire guide which is provided over a proximal end side of the operation wire, and a portion of which is fixed to the insertion tube portion; a distal end side abutting portion provided at a proximal end of the distal end side wire guide; and a proximal end side abutting portion which is provided at a distal end of the proximal end side wire guide, and brought into abutment with the distal end side abutting portion when the operation wire is moved backward so that the bending portion is bent.

BRIEF DESCRIPTION OF THE SEVERAL VIEWS OF THE DRAWINGS

The accompanying drawings, which constitute a part of the specification, illustrate embodiments of the invention, and together with the general description given above and the detailed description of the embodiments given below, serve to explain the principles of the invention.

DETAILED DESCRIPTION OF THE INVENTION

A first embodiment of the invention will be explained hereinafter with reference to FIGS. 1 to 6B.

Figure 1:
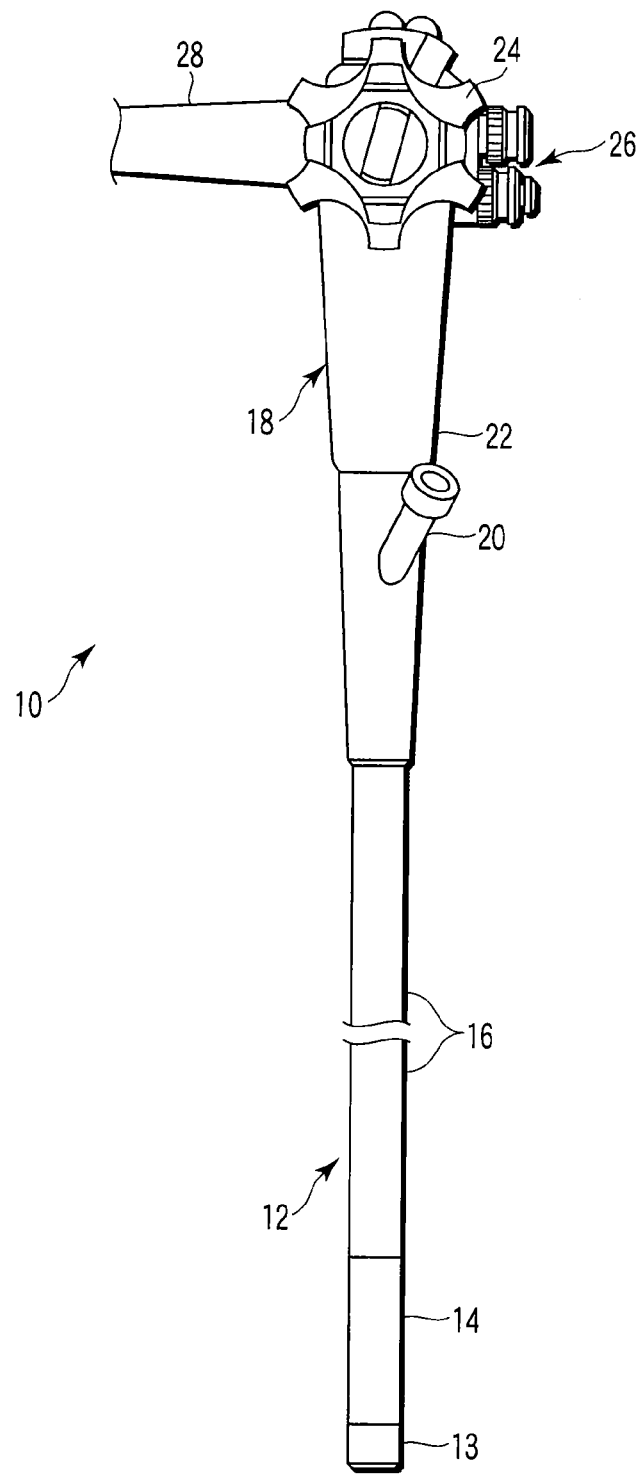
FIG. 1 is a perspective view showing an endoscope according to a first embodiment of the invention.

Referring to FIG. 1, an endoscope 10 according to the embodiment includes an elongated insertion portion 12 to be inserted into a body cavity. The insertion portion 12 is formed by connecting a distal end rigid portion 13, a bending portion 14 to be operated to be bent and a long insertion tube portion 16, sequentially from the distal end side. A control portion 18 held and operated by an operator is connected to the proximal end of the insertion portion 12. In the distal end portion of the control portion 18, an accessory insertion inlet 20 for inserting an accessory is provided. The middle portion of the control portion 18 is a grip portion 22 to be gripped by an operator. In the proximal end part of the control portion 18, a bending operation knob 24 for operating the bending portion 14 to be bend and an air/water supply button 26 for supplying air and water from the distal end of the insertion portion 12 are provided. A universal cable 28 is extended from the proximal end of the control portion 18. The universal cable 28 connects the endoscope 10 to a light source apparatus, a video processor, and an air/water supply apparatus.

Figure 2:
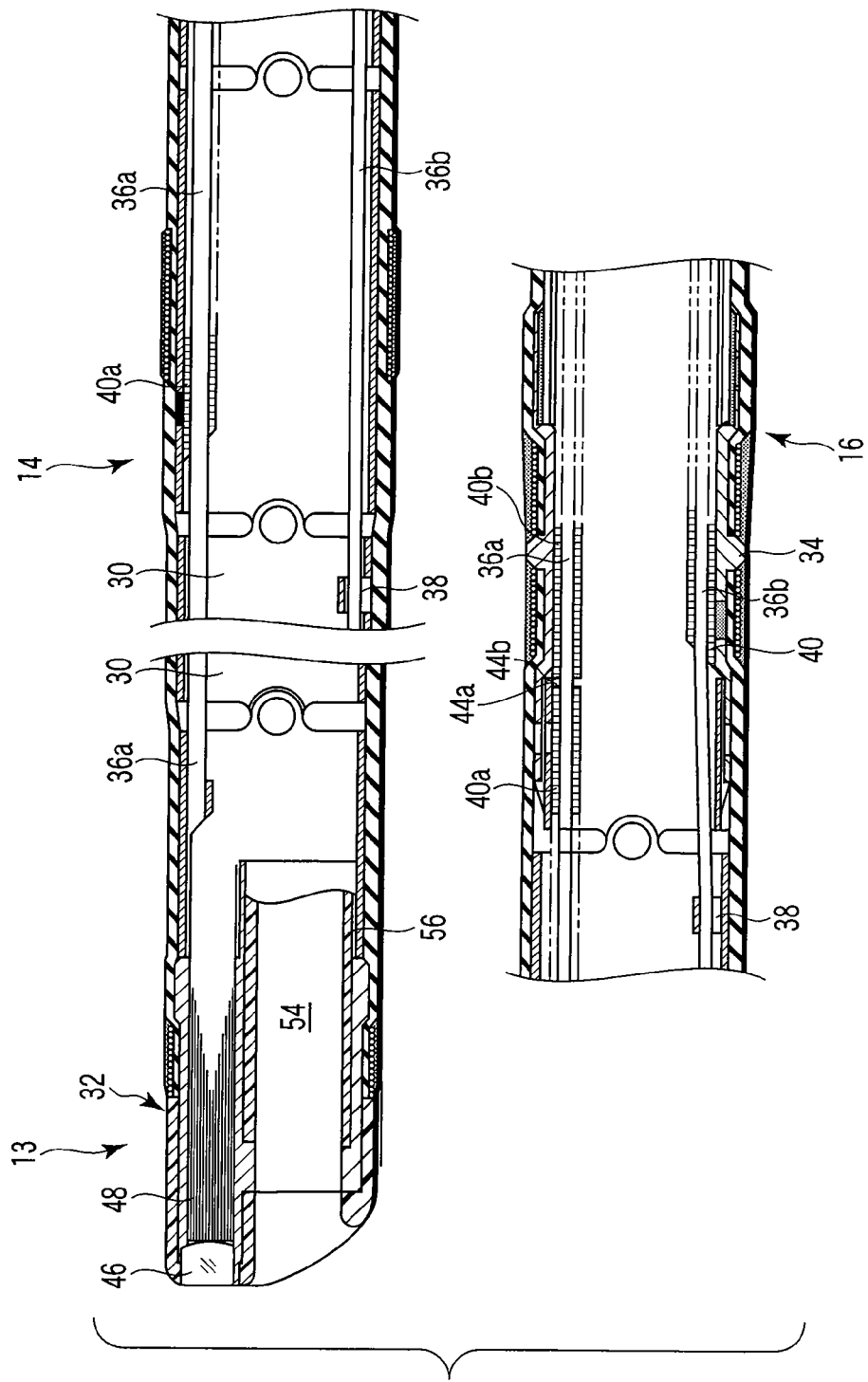
FIG. 2 is a longitudinal cross-sectional view showing an insertion portion of the endoscope according to the first embodiment of the invention.
Figure 3:
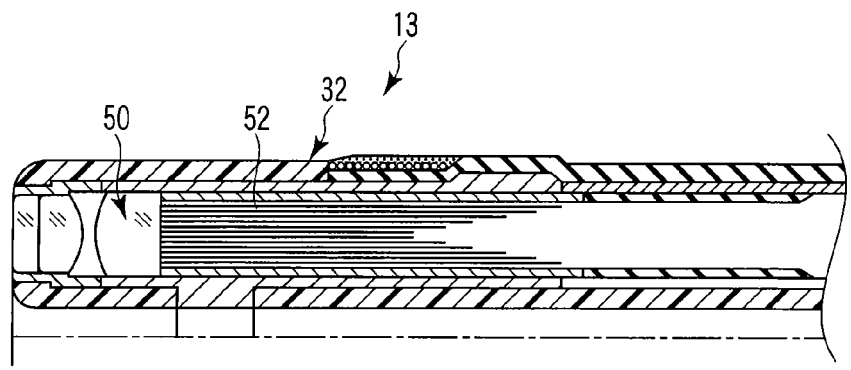
FIG. 3 is a longitudinal cross-sectional view showing an observation optical system of the insertion portion of the endoscope according to the first embodiment of the invention.

The bending mechanism of the bending portion 14 will be explained with reference to FIGS. 1 to 3.

A number of substantially cylindrical bending parts 30 are provided side by side, rotatably and coaxially to each other in the bending portion 14. Namely, a pair of tongue pieces is projected symmetrically to the central axis of the bending part 30 at both end faces of each bending part 30, and a pair of tongue pieces of both of adjacent bending parts 30 are overlaid and rotatably connected with rivets to each other. The rotating direction of a pair of adjacent bending parts 30 common to each pair of adjacent bending parts 30, and the bending portion 14 can be bent in two i.e. up-and-down directions. The distal end bending part 30 is connected to a distal end rigid member 32 forming a distal end rigid portion 13, and the proximal end bending part 30 is connected to a connection ring 34 of the distal end portion of the insertion tube portion 16.

An upward operation wire 36a and downward operation wire 36b to operate the bending portion 14 to be bent up and down are inserted through the insertion portion 12.

The distal end of the upward operation wire 36a is fixed to the distal end bending part 30. The upward operation wire 36a is inserted through and guided along a wire insertion hole 38 formed generally in the upper position in the bending part 30. The upward operation wire 36a is inserted through a distal end side wire guide 40a in the proximal end side of the bending portion 14, and inserted through a proximal end side wire guide 40b in the insertion tube portion 16. In the embodiment, a coil sheath is used for the distal end side wire guide 40a and proximal end side wire guide 40b. A resin tube may be used instead of the wire guide 40. The distal end of the distal end side wire guide 40a is fixed to the inside surface of the bending part 30 at the middle of the bending portion 14. The distal end of the proximal end side wire guide 40b is fixed to the inside surface of the connection ring 34 in the distal end portion of the insertion tube portion 16.

At the proximal end of the distal end side wire guide 40a and at the distal end of the proximal end side wire guide 40b, a distal end side flat portion 44a and a proximal end side flat portion 44b substantially perpendicular to the longitudinal direction of the upward operation wire 36a are provided as a distal end side abutting portion and a proximal end side abutting portion, respectively. In the embodiment, the distal end side flat portion 44a and proximal end side flat portion 44b are formed by applying solder or adhesive to a part of a coil sheath, hardening the solder or adhesive, cutting this part, and processing the cut surface to be flat. Epoxy resin is preferable as adhesive. The distal end side flat portion 44a and proximal end side flat portion 44b are usually separated very little (shown emphasizing a clearance in FIG. 2). When the upward operation wire 36a is moved backward, the distal end side flat portion 44a and proximal end side flat portion 44b abut to each other, and connect the distal end side wire guide 40a and proximal end side wire guide 40b. As a result, the distal end side wire guide 40a and proximal end side wire guide 40b function as a tension rod, and prevents bending of the bending portion 14. Therefore, the bending portion 14 is not bent in the upward direction in the proximal end side where the distal end side wire guide 40a is provided. In this way, by the backward movement of the upward operation wire 36a, the bending portion 14 is bent upward with a relatively small radius of curvature.

The distal end of the downward operation wire 36b is also fixed to the distal end bending part 30. In the bending portion 14, the downward operation wire 36b is inserted through the wire insertion hole 38 formed generally at a lower position in the bending part 30. In the insertion tube portion 16, the downward operation wire 36b is inserted through a wire guide 40. In the embodiment, a coil sheath is used for the wire guide 40. The distal end of the wire guide 40 is fixed to the inside surface of the ring 34 in the distal end portion of the insertion tube portion 16. When the downward operation wire 36b is moved backward, the distal end side wire guide 40a of the upward operation wire 36a is moved following the bending part 30 where the distal end side wire guide 40a is fixed, without being pulled by the proximal end side wire guide 40b, and the whole bending portion 14 is bent downward. In this way, by the backward movement of the downward operation wire 36b, the bending portion 14 is bent downward with a relatively large radius of curvature.

The other built-in members of the insertion portion 12 will be explained hereinafter.

In the distal end face portion of the distal end rigid portion 13, an illumination lens 46 is mounted with its distal end face exposed. The distal end of a light guide 48 for transmitting illumination light is connected to the proximal end face of the illumination lens 46. The light guide 48 is inserted through the insertion portion 12, control portion 18 and universal cable 28, and connected to the light source apparatus, so that the illumination light is transmitted from the light source apparatus to the illumination lens 46 through the light guide 48.

In the distal end face portion of the distal end rigid portion 13, an objective lens system 50 is mounted with its distal end face exposed. The distal end of an image guide 52 for transmitting an observation image is connected to the proximal end face of the objective lens system 50. The image guide 52 is inserted through the insertion portion 12 and control portion 18, and connected to the image pick up unit in the control portion 18. The image pick up unit pickups an observation image, and outputs an image signal to the video processor through a signal line inserted through the universal cable 28.

The distal end portion of a channel tube 56 forming an accessory channel 54 is fixed to the distal end rigid portion 13. The accessory channel 54 is extended through the insertion portion 12 and control portion 18, and connected to the accessory insertion inlet 20 of the control portion 18. The accessory channel 54 serves also as an air/water supplying channel in the insertion portion 12. Namely, in the control portion 18, the channel tube 56 is branched, and one of the branched tubes is connected to the accessory insertion inlet 20, and the other is inserted through the universal cable 28 and connected to the air/water supplying apparatus.

The bending portion 14 is bent to two directions with different radius of curvatures. The accessory channel 54 is arranged to be placed outside when bending with a small radius of curvature. Namely, the accessory channel 54 is placed underside in the transverse cross-section of the insertion portion 12. Therefore, when the bending portion 14 is bent with a small radius of curvature, the radius of curvature of the accessory channel 54 does not become so small.

Figure 4:
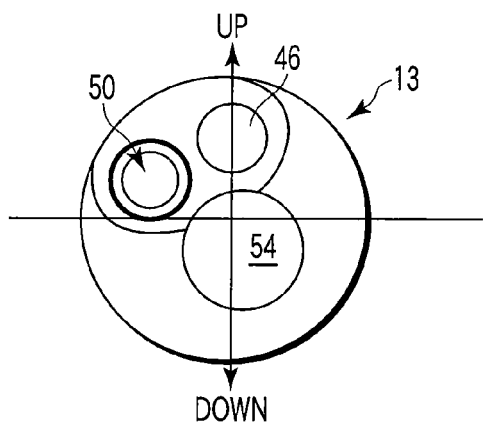
FIG. 4 is a front view showing a distal end rigid portion of the insertion portion of the endoscope according to the first embodiment of the invention.

Referring to FIG. 4, the accessory channel 54 and objective lens system 50 are arranged in the transverse cross-section of the distal end rigid portion 13, so that the distance between the central axis of the accessory channel 54 and objective lens system 50 becomes short in a bending direction. Namely, the accessory channel 54 and objective lens system 50 are not arranged adjacent in the vertical direction, and the objective lens system 50 is arranged in the upper left of the accessory channel 54. Therefore, the projected position of the accessory from the accessory channel 54 comes closer to the central axis of the objective lens system 50, and the accessory comes closer to the center of observation view field in the observation view field.

Figure 5:
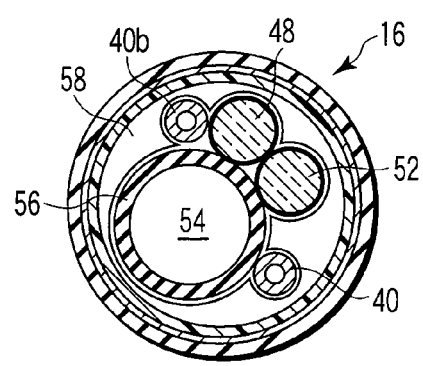
FIG. 5 is a transverse cross-sectional view showing an insertion tube portion of the insertion portion of the endoscope according to the first embodiment of the invention.

Referring to FIG. 5, inside the insertion tube portion 16, stopper members 58 to prevent twisting of the built-in members 48, 52 and 56 are provided at certain intervals in the longitudinal direction of the insertion tube portion 16. The stopper member has a thick cylindrical shape including projections and depressions on the inside surface. The built-in members 48, 52 and 56 are fitted into the projections and recessions, and prevented from twisting. The stopper member 58 may be provided along the total length of the insertion tube portion 16, or the built-in members 48, 52 and 56 may be provided with projections and recessions to prevent twisting.

The inside diameter of the insertion tube portion 16 is gradually increased from the distal end side to the proximal end side. Therefore, in the proximal end side of the insertion tube portion 16, a clearance between the inside surface of the insertion tube and the built-in members 48, 52 and 56 is large.

Next, an explanation will be given on the function of the endoscope insertion portion 12 according to the embodiment.

Figure 6A:
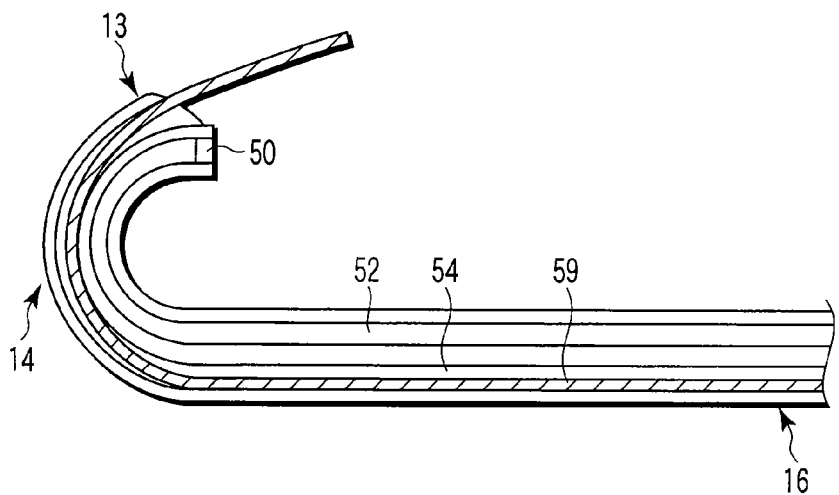
FIG. 6A is a schematic view showing a bending operation with a relatively small radius of curvature of the bending portion of the endoscope according to the first embodiment of the invention.

Referring to FIG. 6A, when bending the bending portion 14 in the upward direction, the bending operation knob 24 is operated, and the upward operation wire 36a is moved backward. As a result, the distal end side flat portion 44a of the distal end side wire guide 40a abuts the proximal end side flat portion 44b of the proximal end side wire guide 40b, and both wire guides are connected. When the upward operation wire 36a is moved further backward, the distal end side wire guide 40a and proximal end side wire guide 40b function as a tension rod. Therefore, the bending portion 14 is not bent in the proximal end side where the distal end side wire guide 40a is provided, and bent in the distal end side where the distal end wire guide 40a is not provided. In this way, the bending portion 14 is bent upward with a relatively small radius of curvature.

Figure 6B:
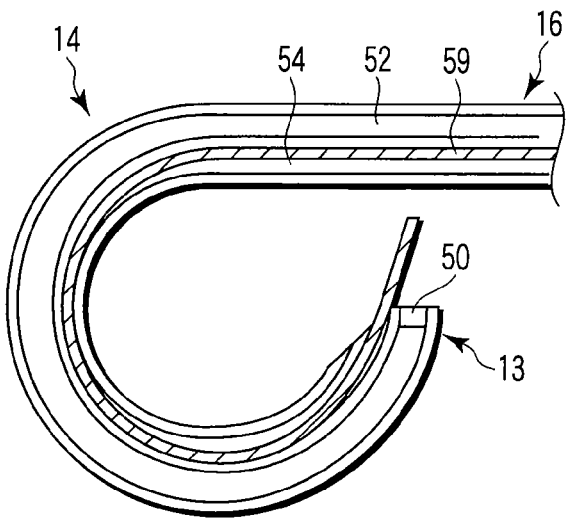
FIG. 6B is a schematic view showing a bending operation with a relatively large radius of curvature of the bending portion of the endoscope according to the first embodiment of the invention.

Referring to FIG. 6B, when bending the bending portion 14 in the downward direction, the bending operation knob 24 is operated, and the downward operation wire 36b is moved backward, and the whole bending portion 14 is bend in the downward direction. This time, the distal end side wire guide 40a is moved following the bending part 30 fixed to the distal end side wire guide 40a without being pulled by the proximal end side wire guide 40b, and the distal end side wire guide 40a is not moved toward the central axis of the bending portion 14. In this way, the bending portion 14 is bent downward with a relatively large radius of curvature.

The distal end side wire guide 40a is not configured to be pushed into the insertion portion 12, and does not generate a repulsive force against push. Therefore, the bending portion 14 is not unnecessarily bent by the repulsive force.

When the bending portion 14 is bent, the built-in members 48, 52 and 56 with the distal ends fixed to the distal end rigid portion 13 are moved forward and backward in the axial direction of the insertion portion 12 inside the insertion portion 12. As the inside diameter of the insertion tube portion 16 is gradually increased from the distal end side to the proximal end side and the clearance between the inside surface of the insertion tube and the built-in members 48, 52 and 56 is large in the proximal end side, the built-in members 48, 52 and 56 can be moved forward and backward smoothly inside the insertion portion 12. As twisting of the built-in members 48, 52 and 56 is prevented by the stopper member 58 in the insertion tube portion 16, the built-in members 48, 52 and 56 are rarely twisted during forward/backward movements, and the built-in members 48, 52 and 56 are moved forward and backward more smoothly inside the insertion portion 12.

When treating an affected part under endoscopic observation, the accessory 59 is inserted into the accessory insertion inlet 20, passed through the accessory channel 54, and then the distal end of the accessory 59 is projected from the distal end rigid portion 13. When the bending portion 14 is bent upward, the radius of curvature of the bending portion 14 becomes relatively small, but as the accessory channel 54 is placed outside, the radius of curvature of the accessory channel 54 becomes not so small. Therefore, the accessory 59 can be inserted smoothly from the proximal end side to the distal end side of the bending portion 14 and, when the bending portion 14 is bent with the accessory 59 inserted through the bending portion, excessive force is not applied to the accessory 59.

The distal end portion of the accessory 59 is projected from the distal end rigid portion 13, and the treatment is performed while the accessory 59 and the affected part are observed. The inside diameter of the accessory channel 54 is greater than the outside diameter of the accessory 59, and when the bending portion 14 is bent, the accessory 59 is not projected parallel toward the central axis of the insertion portion 12 and obliquely projected by the force of the accessory 59 returning itself straight. When the bending portion 14 is bent downward and the accessory channel 54 is placed inside, the accessory 59 is projected close to the center of the observation view field of the objective lens system 50 arranged more inside than the accessory channel 54 (FIG. 6B). On the other hand, when the bending portion 14 is bent upward and the accessory channel 54 is placed outside, the accessory 59 is projected separating from the center of the observation view field of the objective lens system 50 (FIG. 6A). The distance between the central axis of the accessory channel 54 and objective lens system is short in the bending direction, and the projected position of the accessory 59 from the accessory channel 54 closes to the central axis of the objective lens system 50. Therefore, even if the accessory 59 is projected separating from the center of the observation view field of the objective lens system 50, the accessory 59 is not extremely separated from the center of the observation view field.

The endoscope insertion portion 12 according to the embodiment provides the following effects.

In the endoscope insertion portion 12 according to the embodiment, when the bending portion 14 is bent by moving the upward operation wire 36a backward, the distal end side flat portion 44a and proximal end side flat portion 44b abut to each other, and the distal end side wire guide 40a functions as a tension rod and prevents bending of the bending portion 14. When the upward operation wire is moved forward, the distal end side wire guide 40a is moved without being pulled by the proximal end side wire guide 40b, and the distal end side wire guide 40a is prevented from moving toward the central axis of the bending portion 14. Further, the distal end side wire guide 40a is not configured to be pushed into the insertion portion 12, and the bending portion 14 is prevented from being unnecessarily bent by a repulsive force against push generated in the distal end side wire guide 40a. In the endoscope insertion portion 12 according to the embodiment, necessary and appropriate bending operation is possible, and the built-in members 48, 52, and 56 are prevented from being damaged.

The distal end side flat portion 44a and proximal end side flat portion 44b abutting to each other are substantially perpendicular to the longitudinal direction of the upward operation wire 36a, and they are rarely displaced when abutting to each other, compared with the case where they are inclined to the longitudinal direction. Therefore, the tension rod function of the distal end side wire guide 40a and proximal end side wire guide 40b is sufficiently ensured.

The distal end side flat portion 44a and proximal end side flat portion 44b are formed by using solder or adhesive, and an attachment mechanism can be omitted, compared with the case where these portions are formed by attaching a separate member to the distal end side wire guide 40a and proximal end side wire guide 40b. Therefore, upsizing of the distal end side flat portion 44a and proximal end side flat portion 44b can be avoided.

Particularly, when the wire guide 40 is made of a coil sheath, if the coil sheath is simply cut, the cut portion of the wire is exposed, and the cut portion of the coil sheath cannot be used for the abutting portion. In contrast, an optimum abutting portion can be obtained by applying solder or adhesive to a portion of a coil sheath, hardening the solder or adhesive, cutting this portion, and processing the cut surface to be flat.

The inside diameter of the insertion tube portion 16 is gradually increased from the distal end side to the proximal end side, and the clearance between the inside surface of the insertion tube and the built-in members 48, 52 and 56 is large in the proximal end side of the insertion tube portion 16. Further, in the insertion tube portion 16, the stopper member 58 is used to prevent twisting of the built-in members 48, 52 and 56. Therefore, when the bending portion 14 is bent, the built-in members 48, 52 and 56 can be moved forward and backward smoothly in the insertion portion 12, mutual friction of the built-in members 48, 52 and 56 and breakage of the built-in members 48, 52 and 56 are avoided, and the built-in members 48, 52 and 56 are prevented from being damaged during the bending operation.

The accessory channel 54 is placed outside when the bending portion 14 is bent with a small radius of curvature, and the radius of curvature of the accessory channel 54 does not become so small. Therefore, when the bending portion 14 is bent, the accessory 59 can be inserted smoothly, and excessive force is not applied to the accessory 59.

The distance between the central axis of the accessory channel 54 and objective lens system 50 is short in the bending direction. When the bending portion 14 is bent and the accessory channel 54 is placed outside, the accessory 59 is projected separating from the center of the observation view field of the objective lens system 50, but as the projected position of the accessory 59 from the accessory channel 54 is close to the central axis of the objective lens system 50, the accessory 59 is not greatly separated from the center of the observation view field. Therefore, the accessory 59 can be visually confirmed securely.

In the embodiment, when the bending portion 14 is bent with a small radius of curvature, the accessory channel 54 is placed outside, and the radius of curvature of the accessory channel 54 does not becomes so small. Instead, the image guide 52 may be arranged to be placed outside when the bending portion 14 is bent with a small radius of curvature, so that the radius of curvature of the image guide 52 does not become so small. In this case, it is possible to protect the image guide 52, which is relatively easily damaged by the bending and the function is degraded by the damage.

Figure 7:
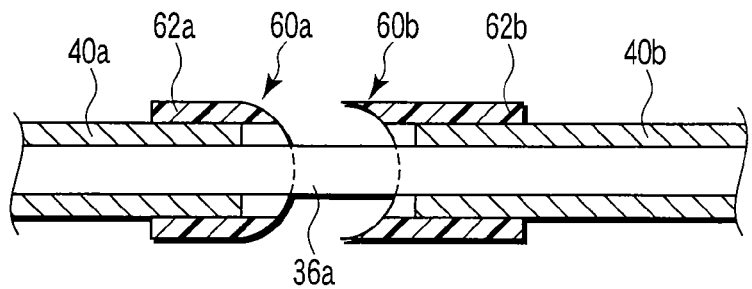
FIG. 7 is a longitudinal cross-sectional view showing a distal end side wire guide and a proximal end side wire guide of an endoscope according to a second embodiment of the invention.

FIG. 7 shows a second embodiment of the invention. The components having the same functions as those of the first embodiment are given the same reference numbers, and explanation will be omitted.

In the embodiment, as the distal end side abutting portion and the proximal end side abutting portion, a distal end engaging portion 60a and a proximal end engaging portion 60b abutting and engaging to each other are used. These distal end side engaging portion 60a and proximal end side engaging portion 60b are formed by providing a substantially cylindrical distal end side engaging member 62a and proximal end side engaging member 62b as a distal end side abutting member and a proximal end side abutting member, respectively over the proximal end of the distal end side wire guide 40a and the distal end of the proximal end side wire guide 40b and fixing them thereto. The proximal end of the distal end side engaging portion 60a is shaped like a semicircular projection, and the distal end of the proximal end side engaging portion 60b is shaped like a semicircular recession. When the upward operation wire 36a is moved backward, the projection and recession are engaged to each other, and the wire guides 40a and 40b are connected.

The endoscope insertion portion 12 according to the embodiment provides the following effects.

In the endoscope insertion portion 12 according to the embodiment, the distal end side engaging portion 60a and proximal end side engaging portion 60b are engaged to each other when abutting, and the distal end side engaging portion 60a and proximal end side engaging portion 60b are sufficiently prevented from being displaced when abutting. Therefore, the function as a tension rod of the distal end side wire guide 40a and proximal end side wire guide 40b is ensured.

As the distal end side engaging portion 60a and proximal end side engaging portion 60b are formed by providing the distal end side engaging member 62a and proximal end side engaging member 62b, respectively at the ends of the distal end side wire guide 40a and proximal end side wire guide 40b, complex shaped distal end side engaging portion 60a and proximal end side engaging portion 60b can be easily formed.

Figure 8:
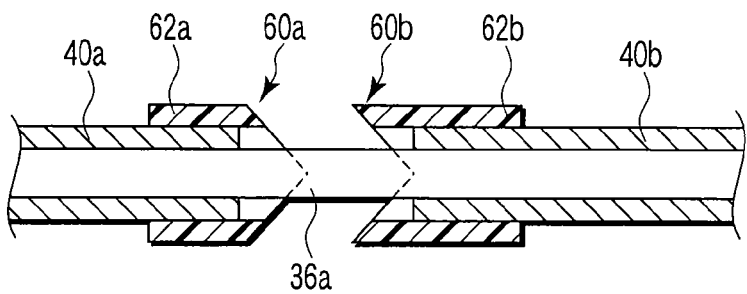
FIG. 8 is a longitudinal cross-sectional view showing a distal end side wire guide and a proximal end side wire guide of an endoscope of a modification of the second embodiment of the invention.

FIG. 8 shows a modification of the second embodiment of the invention. In this modification, the proximal end of the distal end side engaging portion 60a is shaped like a triangular projection, and the distal end of the proximal end side engaging portion 60b is shaped like a triangular recession. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope insertion portion comprising:
   an insertion tube portion including a distal end portion and a proximal end portion;
   a bending portion including a middle portion and a proximal end portion connected to the distal end portion of the insertion tube portion;
   a first operation wire inserted through the bending portion and insertion tube portion, and configured to be operated to be moved forward and backward to operate the bending portion to be bent in a first direction;
   a second operation wire inserted through the bending portion and insertion tube portion, arranged opposite to the first operation wire, and configured to be operated to be moved forward and backward to operate the bending portion to be bent in a second direction opposite to the first direction;
   a distal end side wire guide provided over a distal end side of the first operation wire, including a distal end portion fixed to the middle portion of the bending portion and a proximal end portion, and extending from the middle portion of the bending portion to the proximal end portion of the bending portion;
   a proximal end side wire guide provided over a proximal end side of the first operation wire, including a distal end portion fixed to the distal end portion of the insertion tube portion, and extending from the distal end portion of the insertion tube portion toward the proximal end portion of the insertion tube portion;

a distal end side abutting portion provided at the proximal end portion of the distal end side wire guide; and a proximal end side abutting portion provided at the distal end portion of the proximal end side wire guide, and configured to be brought into abutment with the distal end side abutting portion when the first operation wire is moved backward so that the bending portion is bent.

2. The endoscope insertion portion according to claim 1, wherein the distal end side abutting portion and the proximal end side abutting portion are formed by a distal end side flat portion and a proximal end side flat portion substantially perpendicular to a longitudinal direction of the first operation wire and configured to be brought into abutment to each other.

3. The endoscope insertion portion according to claim 1, wherein the distal end side abutting portion and the proximal end side abutting portion are formed by a distal end side engaging portion and a proximal end side engaging portion configured to be brought into abutment and engaged to each other.

4. The endoscope insertion portion according to claim 1, wherein at least one of the distal end side abutting portion and the proximal end side abutting portion is formed by using solder or adhesive.

5. The endoscope insertion portion according to claim 1, wherein at least one of the distal end side abutting portion and the proximal end side abutting portion is formed by providing an abutting member.

6. The endoscope insertion portion according to claim 1, wherein the distal end side wire guide and the proximal end side wire guide are configured to be connected to each other and function as a tension rod, and a proximal end side portion of the pending portion in which the distal end side wire guide is configured not to be operated to be bent in the first direction and a distal end side portion of the bending portion in which the distal end side wire guide is not configured to be operated to be bent in the first direction, when the first operation wire is operated to be moved backward, and the whole bending portion is configured to be operated to be bent in the second direction, and the distal end side wire guide is configured to be moved following the middle portion of the bending portion to which the distal end portion of the distal end side wire guide is fixed without being pulled by the proximal end side wire guide, when the second operation wire is operated to be moved backward.

7. An endoscope comprising an endoscope insertion portion including:

an insertion tube portion including a distal end portion and a proximal end portion;

a bending portion including a middle portion and a proximal end portion connected to the distal end portion of the insertion tube portion;

a first operation wire inserted through the bending portion and insertion tube portion, and configured to be operated to be moved forward and backward to operate the bending portion to be bent in a first direction;

a second operation wire inserted through the bending portion and insertion tube portion, arranged opposite to the first operation wire, and configured to be operated to be moved forward and backward to operate the bending portion to be bent in a second direction opposite to the first direction;

a distal end side wire guide provided over a distal end side of the first operation wire, including a distal end portion fixed to the middle portion of the bending portion and a proximal end portion, and extending from the middle portion of the bending portion to the proximal end portion of the bending portion;

a proximal end side wire guide provided over a proximal end side of the first operation wire, including a distal end portion fixed to the distal end portion of the insertion tube portion, and extending from the distal end portion of the insertion tube portion toward the proximal end portion of the insertion tube portion;

a distal end side abutting portion provided at the proximal end portion of the distal end side wire guide; and a proximal end side abutting portion provided at the distal end portion of the proximal end side wire guide, and configured to be brought into abutment with the distal end side abutting portion when the first operation wire is moved backward so that the bending portion is bent in the first direction.

8. The endoscope according to claim 7, wherein the distal end side abutting portion and the proximal end side abutting portion are formed by a distal end side flat portion and a proximal end side flat portion substantially perpendicular to a longitudinal direction of the first operation wire and configured to be brought into abutment to each other.

9. The endoscope according to claim 7, wherein the distal end side abutting portion and the proximal end side abutting portion are formed by a distal end side engaging portion and a proximal end side engaging portion configured to be brought into abutment and engaged to each other.

10. The endoscope according to claim 7, wherein at least one of the distal end side abutting portion and the proximal end side abutting portion is formed by using solder or adhesive.

11. The endoscope according to claim 7, wherein at least one of the distal end side abutting portion and the proximal end side abutting portion is formed by providing an abutting member.

12. The endoscope according to claim 7, wherein the distal end side wire guide and the proximal end side wire guide are configured to be connected to each other and function as a tension rod, and a proximal end side portion of the bending portion in which the distal end side wire guide is configured not to be operated to be bent in the first direction and a distal end side portion of the bending portion in which the distal end side wire guide is not configured to be operated to be bent in the first direction, when the first operation wire is operated to be moved backward, and the whole bending portion is configured to be operated to be bent in the second direction, and the distal end side wire guide is configured to be moved following the middle portion of the bending portion to which the distal end portion of the distal end side wire guide is fixed without being pulled by the proximal end side wire guide, when the second operation wire is operated to be moved backward.

* * * * *